United States Patent
Branch et al.

(10) Patent No.: US 11,065,277 B2
(45) Date of Patent: Jul. 20, 2021

(54) METHOD OF AMELIORATING SIDE EFFECTS OF SICKLE CELL DISEASE TREATMENTS

(71) Applicant: ALBERT EINSTEIN COLLEGE OF MEDICINE, Bronx, NY (US)

(72) Inventors: Craig Branch, Cornwall, NY (US); Seetharama Acharya, Cresskill, NJ (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 15/774,763

(22) PCT Filed: Nov. 8, 2016

(86) PCT No.: PCT/US2016/060952
§ 371 (c)(1),
(2) Date: May 9, 2018

(87) PCT Pub. No.: WO2017/083281
PCT Pub. Date: May 18, 2017

(65) Prior Publication Data
US 2018/0369281 A1 Dec. 27, 2018

Related U.S. Application Data

(60) Provisional application No. 62/252,622, filed on Nov. 9, 2015.

(51) Int. Cl.

| | | |
|---|---|---|
| *A61K 35/14* | (2015.01) |
| *A61K 38/42* | (2006.01) |
| *A61K 31/17* | (2006.01) |
| *A61K 31/341* | (2006.01) |
| *A61K 47/60* | (2017.01) |
| *A61K 31/437* | (2006.01) |
| *A61K 31/352* | (2006.01) |
| *A61K 31/192* | (2006.01) |
| *A61K 31/7048* | (2006.01) |
| *A61P 7/00* | (2006.01) |
| *A61K 9/00* | (2006.01) |
| *A61K 31/353* | (2006.01) |
| *A61K 38/38* | (2006.01) |
| *A61K 45/06* | (2006.01) |

(52) U.S. Cl.
CPC ............ *A61K 35/14* (2013.01); *A61K 9/0053* (2013.01); *A61K 31/17* (2013.01); *A61K 31/192* (2013.01); *A61K 31/341* (2013.01); *A61K 31/352* (2013.01); *A61K 31/353* (2013.01); *A61K 31/437* (2013.01); *A61K 31/7048* (2013.01); *A61K 38/38* (2013.01); *A61K 38/42* (2013.01); *A61K 45/06* (2013.01); *A61K 47/60* (2017.08); *A61P 7/00* (2018.01)

(58) Field of Classification Search
None
See application file for complete search history.

(56) References Cited

U.S. PATENT DOCUMENTS

| | | | | |
|---|---|---|---|---|
| 7,119,208 | B2 * | 10/2006 | Safe ..................... | C07D 307/46 546/280.4 |
| 7,144,989 | B2 * | 12/2006 | Acharya ............... | C07C 331/28 530/385 |
| 2009/0197969 | A1 | 8/2009 | Poulsen et al. | |
| 2009/0298746 | A1 * | 12/2009 | Acharya ............... | A61K 38/00 514/1.1 |
| 2013/0261061 | A1 * | 10/2013 | Acharya ............. | C07K 14/765 514/15.2 |
| 2014/0011741 | A1 | 1/2014 | Abuchowski et al. | |

FOREIGN PATENT DOCUMENTS

| | | |
|---|---|---|
| WO | 2015127163 A1 | 8/2015 |
| WO | 2015161220 A1 | 10/2015 |

OTHER PUBLICATIONS

Henneberg et al. "Protective effect of flavonoids against reactive oxygen species production in sickle cell anemia patients treated with hydroxyurea," Rev Bras Hematol Hemoter. 2013;35(1):52-5 (Year: 2013).*

Agrawal et al. ("Hydroxyurea in Sickle Cell Disease: Drug Review," Indian J Hematol Blood Transfus (Apr.-Jun. 2014) 30(2):91-96) (Year: 2014).*

Abdulmalik etal. ("5-hydroxymethyl-2-furfural modifies intracellular sickle haemoglobin and inhibits sickling of red blood cells," British Journal of Haematology, 128, (2005) pp. 552-561) (Year: 2005).*

Hannemann et al. ("Effects of 5-hydroxymethyl-2-furfural on the volume and membrane permeability of red blood cells from patients with sickle cell disease," J Physiol 592.18 (2014) pp. 4039-4049) (Year: 2014).*

PCT International Search Report and Written Opinion dated Jan. 19, 2017 for PCT International Patent Application No. PCT/US2016/60952, 11 pages.

Okoye N C et al., Hydroxyurea Therapy in Sickle Cell Disease: An Alternative Approach to Preoperative Red Cell Transfusion, Journal of the National Medical Association, Jun. 2015, vol. 107, No. 2, pp. 102+103.

Hannemann A et al., Effects of 5-hydroxymethyl-2-furfural on the Volume and Membrane Permeability of Red Blood Cells from Pateints with Sickle Cell Disease, The Journal of Physiology, Aug. 13, 2014, vol. 592, No. 18, pp. 4039-4049.

(Continued)

*Primary Examiner* — Christina Bradley
(74) *Attorney, Agent, or Firm* — Perkins Coie LLP (57) ABSTRACT

A method of reducing a cerebral tissue pathology associated with a sickle cell disease therapy in a subject is provided using (i) a synthetic high-oxygen affinity hemoglobin-containing molecule or (ii) synthetically treated high-oxygen affinity blood.

10 Claims, 6 Drawing Sheets

(56) References Cited

OTHER PUBLICATIONS

Henneberg R et al., Protective Effect of Flavonoids against Reactive Oxygen Species Production in Sickle Cell Anemia Patients Treated with Hydroxyurea, Revista Brasileira de Hemoterapia, 2013, vol. 35, No. 1, pp. 52-55.

* cited by examiner

METHOD OF AMELIORATING SIDE EFFECTS OF SICKLE CELL DISEASE TREATMENTS

CROSS-REFERENCE TO RELATED APPLICATIONS

This application is a U.S. national stage entry under 35 U.S.C. § 371 of PCT International Patent Application No. PCT/US2016/060952, filed Nov. 8, 2016, which claims benefit of U.S. Provisional Application No. 62/252,622, filed Nov. 9, 2015, the contents of each of which are incorporated herein by reference into the subject application.

BACKGROUND OF THE INVENTION

Sickle cell disease (SCD) is an inherited red blood cell disorder in which the affected individual's red blood cells exhibit hemoglobin SS (HbSS) rather than HbAA. SCD is often accompanied by sickle cell vaso-occlusive pathology which occurs when the HbSS undergoes polymerization, resulting in red blood cell "sickling". Sickling and cell lysis associated with SCD leads to endothelial blood cell adhesion, reduced red blood cell deformability and vaso-occlusion. In addition, the shorter half life of sickled red blood cells also leads to anemia. Anemia, complicated by systemic vaso-occlusive disease, contributes to chronic organ hypoxia and elevated (hyperemic) cerebral blood flow.

Human endothelial tissues in the brain and kidney are finely attuned to the delivery of oxygen, accomplished by arterial and arteriolar smooth muscle mechanisms under chemical, neural and myogenic control. Through these mechanism, cerebral blood flow is maintained, or adjusted dynamically and locally to provide adequate oxygen to meet metabolic demand. Nitric oxide (NO) is the primary vaso-active molecule through which adjustments in arterial and arteriolar tone is achieved. In SCD induced anemia (SCA) however, red blood cell concentration decreases, they lose their pseudoplasticity through damage by increased autoxodation of oxyHbSS and polymerization of deoxy HbSS, and, with the damaged cells lysing, this leads to blood borne hydroxyl radicals that scavenge NO. Nonetheless, SCA leads to severe and chronic cerebral blood flow hyperemia, often with complete exhaustion of cerebrovascular auto-regulatory reserves.

Therapies being developed for treating SCD and SCD-vaso-occlusive 'crisis' are directed primarily at resolving red blood cell sickling due to deoxy-HbS polymerization in systemic tissues. Such therapies have the positive effect of reducing activated leukocyte and other cell adhesion to endothelial cells, reversing sickling of red blood cells containing HbS, with the end result that systemic vasculatures are cleared of obstructive constituents, resulting in reversal of systemic blood flow impairment. Clearing of obstructive components from the systemic vasculature leads to rapid increases in capillary filling and improved tissue perfusion throughout the systemic tissues.

When anti-sickling therapeutics are employed, systemic tissue perfusion improves and functional systemic capillary volume increases. Existing antisickling therapies in use (e.g., blood transfusion) clear the systemic tissues of sickled red blood cells, increasing functional systemic capillary volume. Recent findings demonstrate that amelioration of the systemic red blood cell vaso-occlusion associated with these events occur coincidently with significant decreases in cerebral blood flow, resulting in hypoxic compromise of cerebral tissue.

One mechanism by which this may occur is as follows: the successful anti-sickling therapy results in improved systemic tissue perfusion, increased capillary and venous functional volume with the result that a semi-transient drop in mean blood pressure occurs. Since the brain (and perhaps kidney) myogenic vasculature has already been maximally vasodilated to maximize tissue blood flow, flow through these tissues are now solely determined by their perfusion pressure—or mean blood pressure minus venous outflow pressure (which is near 0). Thus the perfusion pressure drops in response to the successful amelioration of vaso-occlusive pathology, resulting a significant reduction in cerebral blood flow. The therapeutic consequent drop in cerebral blood flow lead to increased brain hypoxia and possible cerebral damage. The resulting increase in cerebral deoxyHbS levels can aggravate HbS-red blood cell sickling in the brain and can lead to further ischemic damage, even stroke.

Furthermore, red blood cells containing polymeric HbSS, the culprit in SCD, have lower oxygen affinity than non-sickle red blood cells, and therefore release their oxygen more quickly. This results in more rapid oxygen release in capillary tissues, which may lead to 'downstream' oxygen deprivation in organ tissues.

This invention provides a method of ameliorating unwanted cerebral and renal side-effects of potential sickle cell disease therapeutics, especially those therapeutics directed at improving systemic/peripheral tissue perfusion through reductions in HbSS cell sickling and/or reducing the oxidative stress, or combinations thereof.

SUMMARY OF THE INVENTION

A method is provided for reducing a cerebral tissue pathology associated with a sickle cell disease therapy in a subject comprising administering to the subject who is receiving, has received or will receive the sickle cell therapy, an amount of (i) a synthetic high-oxygen affinity hemoglobin-containing molecule or (ii) synthetically generated high-oxygen affinity blood, sufficient to reduce a cerebral tissue pathology associated with a sickle cell disease therapy in a subject.

Also provided is a method of reducing a cerebral tissue pathology associated with a sickle cell disease therapy in a subject comprising administering to the subject who is receiving, has received or will receive an antisickling or antioxidant sickle cell therapy, an amount of (i) a synthetic high-oxygen affinity albumin-containing molecule and (ii) hydroxyl urea, 5-hydroxyl methyl furfural, tucaresol or 2-hydroxy-6 ((2-(1-isopropyl-1H-pyrazol-5-yl) pyridin-3-yl) methoxy) benzaldehyde (referred to as "GBT 440"), or a composition comprising red blood cells ex vivo treated with 5-hydroxyl methyl furfural, tucaresol or GBT 440, sufficient to reduce a cerebral tissue pathology associated with a sickle cell disease therapy in a subject.

Also provided is a composition comprising synthetically treated-high-oxygen affinity blood that has been treated synthetically with one or more of hydroxyl urea, 5-hydroxyl methyl furfural or tucaresol or 2-hydroxy-6 ((2-(1-isopropyl-1H-pyrazol-5-yl) pyridin-3-yl) methoxy) benzaldehyde referred to as GBT 440, so as to become high oxygen affinity. In an embodiment, the blood has been treated with only one of the listed synthetic treatments.

Further aspects of the invention are apparent from the following description.

DETAILED DESCRIPTION OF THE INVENTION

A method is provided for reducing a cerebral tissue pathology associated with a sickle cell disease therapy in a subject comprising administering to the subject who is receiving, has received or will receive the sickle cell therapy, an amount of (i) a synthetic high-oxygen affinity hemoglobin-containing molecule or (ii) synthetically generated high-oxygen affinity blood, sufficient to reduce a cerebral tissue pathology associated with a sickle cell disease therapy in a subject. In an embodiment, the sickle cell therapy is an anti-sickling or antioxidant or anti-adhesive sickle cell therapy. In an embodiment, the sickle cell therapy is an anti-sickling therapy. In an embodiment, the sickle cell therapy is an antioxidant therapy. In an embodiment, the sickle cell therapy is an anti-adhesive therapy. In an embodiment, the sickle cell therapy is a blood transfusion.

In an embodiment, the cerebral tissue pathology associated with a sickle cell disease therapy is cerebral hypoxic insult. In an embodiment, the synthetic high-oxygen affinity hemoglobin-containing molecule is administered. In an embodiment, the synthetically generated high-oxygen affinity blood is administered. In an embodiment, the synthetic high-oxygen affinity hemoglobin-containing molecule comprises a hemoglobin molecule having 6 molecules of 3,000 mw polyethylene glycol (PEG) attached thereto (P3K6 Hb). In an embodiment, the P3K6 Hb is extension arm facilitated P3K6 Hb (EAF P3K6 Hb). In an embodiment, the P3K6 Hb is an antioxidant adduct of EAF P3K6 Hb. In an embodiment, the antioxidant is a flavonoid. In an embodiment, the method further comprises administering EAF P5K6 recombinant albumin. In an embodiment, the method further comprises administering EAF P5K6 recombinant albumin conjugated with an antioxidant, or a mixture of EAF P5K6 recombinant Alb and antioxidant.

In an embodiment, the sickle cell therapy is an anti-sickling or antioxidant or anti-adhesive sickle cell therapy. In an embodiment, the sickle cell therapy is an anti-sickling therapy. In an embodiment, the sickle cell therapy is an antioxidant therapy. In an embodiment, the sickle cell therapy is an anti-adhesive therapy.

In an embodiment of the methods and compositions described herein, the synthetically treated-high-oxygen affinity blood is "synthetically treated" by virtue of being blood, or a red blood cell containing composition, that has been treated synthetically, e.g. with hydroxyl urea, 5-hydroxyl methyl furfural or tucaresol or 2-hydroxy-6 ((2-(1-isopropyl-1H-pyrazol-5-yl) pyridin-3-yl) methoxy) benzaldehyde referred to as GBT 440, so as to become high-oxygen affinity.

In embodiments of the methods, the blood proteins (albumin or hemoglobin) recited are recombinant.

In an embodiment, the method further comprises administering (i) a synthetic high-oxygen affinity albumin-containing or hemoglobin-containing molecule.

In an embodiment, a method is provided, mutatis mutandis, with P3K6 hemoglobin replaced with one of P5K2 Hb and P10K2 Hb, P5K2 aa-Hb, P5K2 bovine Hb, or p5K4 canine Hb, EAF P5K6 human Hb or EAF P3K6 bovine Hb, EAF P3K6 human Hb with Cys-93(beta) free (not modified) or EAF P3K6 bovine Hb with Cys-92(beta) free (not modified), all of which have higher oxygen affinity than blood and will achieve at least equivalent protection.

In an embodiment, the methods further comprise administering an amount of a quercetin to the subject.

Also provided is a method of reducing a cerebral tissue pathology associated with a sickle cell disease therapy in a subject comprising administering to the subject who is receiving, has received or will receive the sickle cell therapy, an amount of (i) a synthetic high-oxygen affinity albumin-containing molecule and (ii) hydroxyl urea, 5-hydroxyl methyl furfural, or a composition comprising red blood cells ex vivo treated with 5-hydroxyl methyl furfural, sufficient to reduce a cerebral tissue pathology associated with a sickle cell disease therapy in a subject.

In an embodiment, the hydroxyl urea or 5-hydroxyl methyl furfural or tucaresol or GBT 440 is orally administered. In an embodiment, the hydroxyl urea or 5-hydroxyl methyl furfural is administered via a non-oral route. In an embodiment, the cerebral tissue pathology associated with a sickle cell disease therapy is cerebral hypoxic insult. In an embodiment, the hydroxyl urea is administered. In an embodiment, the 5-hydroxyl methyl furfural is administered. In an embodiment, the composition comprising red blood cells ex vivo treated with 5-hydroxyl methyl furfural, tucaresol or GBT-440 is administered. In an embodiment, the synthetic high-oxygen affinity albumin-containing molecule comprises an albumin molecule having 6 molecules of 5,000 mw polyethylene glycol (PEG) attached thereto (P5K6 Alb). In an embodiment, the P5K6 Alb is extension arm facilitated P5K6 Alb (EAF P5K6 Alb). In an embodiment, the P5K6 Alb is an antioxidant adduct of extension arm facilitated P5K6 Alb. In an embodiment, the antioxidant is a flavonoid. In an embodiment, an antioxidant is admin- istered orally to the subject. In an embodiment, the antioxidant is a flavonoid. In an embodiment, the antioxidant is quercetin or isoquercetin.

In an embodiment, quercetin is 2-(3,4-dihydroxyphenyl)-3,5,7-trihydroxy-4H-chromen-4-one.

In an embodiment of the methods and compositions, the composition comprises 4% hexaPEGylated-albumin. In an embodiment of the methods and compositions, the composition administered comprises 1-10% EAF PEGylated-blood protein. In an embodiment of the methods and compositions, the blood protein is covalently bonded to an antioxidant.

In an embodiment of the methods, the SCD therapy is a blood transfusion. In an embodiment, the composition (the hemoglobin-containing molecule or albumin-containing molecule) or synthetically treated blood is administered prior to the blood transfusion, but at one of: less than 30 mins., less than 1 hour, less than 2 hours, less than 5 hours, less than 12 hours, or less than 24 hours before a blood transfusion into the subject. In an embodiment, the composition or synthetically treated blood is administered during a blood transfusion. In an embodiment, the composition or synthetically treated blood is administered subsequent to a blood transfusion into the subject, but at one of: less than 15 mins., less than 30 mins., less than 1 hour, less than 2 hours, less than 5 hours, less than 12 hours, or less than 24 hours subsequent to the blood transfusion into the subject. In an embodiment, the SCD therapy is a not blood transfusion.

In an embodiment of the methods and compositions, the blood protein (with or without EAF PEGylation) is covalently bonded to an antioxidant (an "EAF-PEGylated blood protein antioxidant conjugate" or a "blood protein antioxidant conjugate", respectively). In an embodiment, the blood protein is EAF polynitroxylated. In an embodiment the antioxidant is quercetin. In an embodiment the antioxidant is isoquercetin. In an embodiment, the antioxidant is a thiol, thioether, glutathione, curcumin, N-acetyl methionine, or SOD mimetic (e.g., tempol (1-oxyl-2,2,6,6-tetramethyl-4-hydroxypiperidine) or a proxyl or polysulfide). In an embodiment, the EAF PEGylated blood protein can further comprise one or more of the following molecules:

wherein X is the blood protein, (or its EAF PEGylated form, or their polymeric forms, e.g. nanomaterials), and wherein n is an integer from 1 through 100, and where the antioxidant molecule is any of the species referred to hereinabove in the tempol shown in this structure or in place of the tempol shown.

As used herein a "blood protein", unless otherwise specified, is a protein usually found in the blood of the relevant (mammalian) subject, such as hemoglobin or albumin or, if specified, a derivative thereof, such as a hemoglobin derivative showing an improved or decreased different affinity for oxygen relative to native hemoglobin. In an embodiment, the blood protein is a hemoglobin or an albumin, and includes isolated, purified or recombinant forms of each thereof. In an embodiment, the blood protein is a human hemoglobin. In an embodiment, the blood protein is a human albumin.

In embodiments of the methods and compositions, the PEG may be PEG-3000 through PEG-40,000. In an embodiment, the PEG is selected from PEG-3000, PEG-5000, PEG-7500, PEG 10,000, PEG-15,000, PEG-20,000, PEG-30,000, and/or PEG-40,000, wherein the number refers to the average molecular weight of the PEG. In an embodiment, the PEG geometry may be linear, branched, star, or comb.

PEGylated blood proteins, including albumins and hemoglobins, and methods of synthesis thereof, are also described in U.S. Pat. No. 8,071,546 and in U.S. Patent Application Publication No. US 2009-0298746 A1 and in PCT International Publication No. WO 2011/106086, the contents of each of which are hereby incorporated by reference.

As used herein, an "extension arm facilitated" (EAF) PEGylated protein shall mean a protein having at least one PEG molecule attached thereto via a flexible chemical linker (an extension arm). In an embodiment where a plurality of PEG molecules are each attached via flexible chemical linkers, the extension arm facilitated PEGylated protein is capable of a lower packing density of the attached PEG chains in the PEG-shell than the packing density in the protein to which the PEG chains are linked. In an embodiment, the extension arm (i.e. the flexible small molecular weight aliphatic linker in between the protein and the PEG) is ~1 nm in length.

In an embodiment of the methods and compositions, a EAF PEGylated protein of the invention may be one of the following:

where n is an integer from 1 through 100 and X is a blood protein, such as a hemoglobin or an albumin, and wherein m is the number of ethylene glycol monomers. PEGs of from 1,000 to 40,000 daltons are preferred. The m value can be chosen to provide PEGs of from 1,000 to 40,000 daltons. P3K6 hemoglobin is an embodiment. P5K6 albumin is an embodiment.

In an embodiment, the methods further comprise administering an amount of a quercetin or of an isoquercetin to the subject. In an embodiment, the compositions further comprise an amount of a quercetin or of an isoquercetin.

Also provided is a composition comprising synthetically treated-high-oxygen affinity blood that has been treated synthetically with one or more of hydroxyl urea, 5-hydroxyl methyl furfural or tucaresol or 2-hydroxy-6 ((2-(1-isopropyl-1H-pyrazol-5-yl) pyridin-3-yl) methoxy) benzaldehyde referred to as GBT 440, so as to become high oxygen affinity. In an embodiment, the blood has been treated with only one of the listed synthetic treatments.

Also provided is a composition comprising synthetic high-oxygen affinity blood protein and one or more of hydroxyl urea, 5-hydroxyl methyl furfural or tucaresol or 2-hydroxy-6 ((2-(1-isopropyl-1H-pyrazol-5-yl) pyridin-3-yl) methoxy) benzaldehyde referred to as GBT 440, so as to become high oxygen affinity. In an embodiment, the composition comprises only one of the listed synthetic treatments.

The subject of the methods herein can be a mammal. In different embodiments, the mammal is a mouse, a rat, a cat, a dog, a horse, a sheep, a cow, a steer, a bull, livestock, a primate, or a monkey. The mammal is preferably a human.

Where a numerical range is provided herein, it is understood that all numerical subsets of that range, and all the individual integers contained therein, are also provided as part of the invention. Thus, a blood protein which comprises from 1 to 100 PEG molecules includes the subset of PEGylated blood proteins which comprise 1 to 50 PEG molecules, the subset of PEGylated blood proteins which comprise 10 to 75 PEG molecules, and so forth, as well as a PEGylated blood protein which comprises 6 PEG molecules, a PEGylated blood protein which comprises 7 PEG molecules, a PEGylated blood protein which comprises 8 PEG molecules, up to and including a PEGylated blood protein which comprises 100 PEG molecules.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Existing therapies for resolution of sickling of red blood cells carrying HbSS in patients with sickle cell anemia are at risk for cerebrovascular toxicity (and/or renal ischemic damage) associated with rapid decreases in cerebral (and/or renal) blood flow due to compromised cerebrovascular autoregulation associated with their disease. Overall combination therapies include both the antisickling agent or antioxidant agents or antiadhesive agents and additional agents that target an increased oxygen delivering capacity of the blood to hypoxic areas are required to protect the brain from cerebrovascular insults (and/or protect from renal damage)

Developing therapies for treating SCD are directed primarily at resolving red blood cell sickling due to dexoy-HbS polymerization or increased autoxidation of oxy-HbS and/or increased oxidative stress or increased adhesion to endothelium. Such therapies have shown the positive effect of reducing activated leukocyte and other cell adhesion to endothelial cells, reversing sickling of red blood cells containing HbS, with the end result that venous vasculature in peripheral and other tissues are cleared of obstructive constituents (sludging of the venous vasculature bed). Most of the therapies advanced seem to achieve the desired attenuation of systemic blood flow impairment characteristic of SCD and painful crisis. This improvement in systemic tissue perfusion occurs rapidly, leading to rapid increases in capillary filling and improved tissue perfusion throughout the peripheral tissue bed.

Many such therapies have been advanced and have shown therapeutic efficacy in transgenic mouse models of sickle cell disease or ex vivo models of the aspects of the pathophysiology of sickle cell disease, but have failed in clinical trials of the advanced therapeutic in clinical trials. This has been a mystery in the design and development of new therapies for sickle cell diseases and other anemias as well. One exception to that has been hydroxyurea that induces the production of fetal Hb, a high oxygen affinity Hb.

Figure 1:
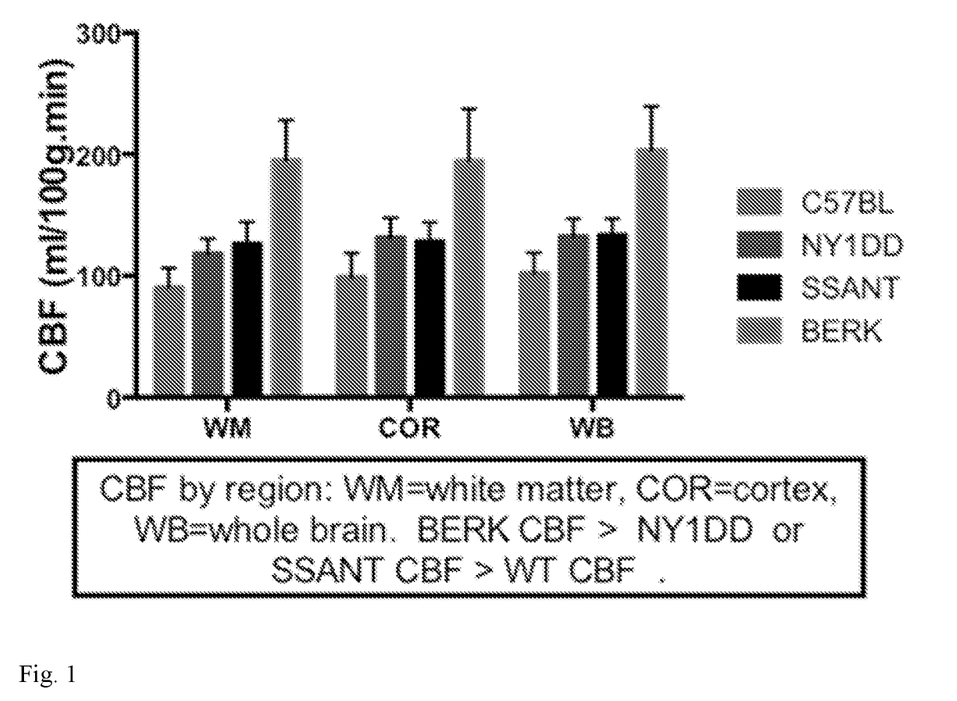
FIG. 1: Increasing CBF associated with severity of sickle cell anemia. BERK mice (Gray bars) expresses human HbS exclusively, resulting in severe hyperemia, cerebral hypoxic ischemia and frequent stroke.

However, herein it is disclosed that in the brain a normal response to the chronic hypoxic insult imposed by sickle cell disease induced anemia, combined with chronically increased circulatory inflammatory constituents resulting from ongoing red blood cell lyses, is severe hyperemia which occurs in excess of that expected by the anemia itself (FIG. 1). In the a very severe transgenic mouse model of sickle cell disease, it is reflected as a very high CBF. The resultant hyperemia often leads to complete exhaustion of the ability of cerebrovascular endothelial tissues to undergo further vasodilatation, and this exhaustion of cerebrovascular reserves is further compromised by ongoing rapid scavenging of nitric oxide by blood-borne hydroxyl radicals associated with lysed sickled red blood cells.

When therapies directed toward resolving systemic impairment of blood flow with or without acute crisis (SCA painful crisis) are successful (as discussed above), the resultant rapid increases in functional capillary volume leads to rapid decreases in arterial blood pressure. Mean arterial blood pressure (MAP) is the primary driving force to overcome cerebrovascular resistance (CVR) and maintain an adequate level of cerebral blood flow (CBF): CBF=MAP/CVR. In SCD, CVR is minimal, due to maximally vasodilated cerebral vasculature tissues. Thus, further vasodilation is not possible to compensate for the decreased MAP resulting from treatment to reverse peripheral vasculature sludging. This results in a consequent drop in CBF leading to worsening hypoxia in cerebral tissues, which leads to hypoxic insults to brain tissue. The resulting increase in cerebral deoxyHbS levels can aggravates HbS-red blood cell sickling, and can lead to further ischemic damage, even stroke.

Accordingly, therapies directed primarily at improving peripheral tissue perfusion through attenuation of the blood flow impairment (through reductions in cell sickling or reductions in oxidative stress or through attenuation of adhesion to endothelium) must take into consideration the need to protect cerebral tissues from further ischemic damage. This protection can be achieved by either maintaining cerebral perfusion against the drop in MAP following rapid decreases in cell sickling, (i) by delivering additional oxygen to brain tissues (i.e., increasing blood oxygen carrying/delivering capacity) particularly targeting the oxygenation of the hypoxic areas or (ii) improving the oxygen-extraction capability of the brain while reducing the potential of HbS to sickle at elevated deoxy-Hb levels.

Figure 2:
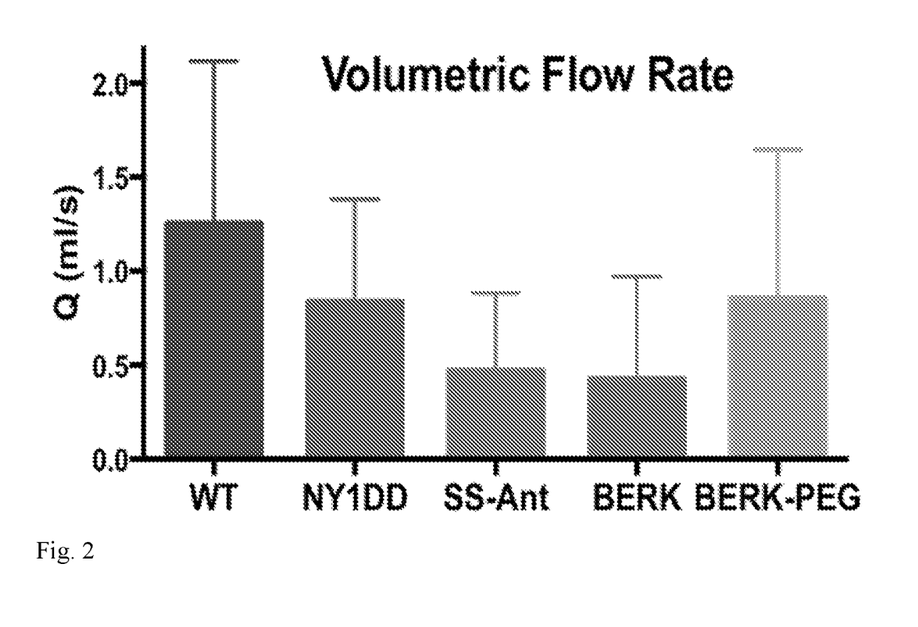
FIG. 2: Volumetric Flow Rate determined from Intravital microscopy in several SCD mouse models. Shear rate and volume flow rate decreased concomitantly with increasing severity of SCD pathology.) (p<0.001; WT>NY1DD, S+S Antilles or BERK). AFTER 10% Topload with EAF-P5K6-Alb, Shear Rate and FLOW both increased in BERK mice, in contrast to the brain, where perfusion decreased.

An example of this effect is exhibited by the supra-perfusion therapy of Extended Arm Facilitated PEGylated Albumin ("EAF-PEG-Albumin" or "EAF-PEG-Alb"). In the systemic circulation, administration of the drug reduces sickling and leukocyte adhesion and results in a large improvement in tissue blood flow (FIG. 2, BERK animal response to BERK-PEG).

Figure 3:
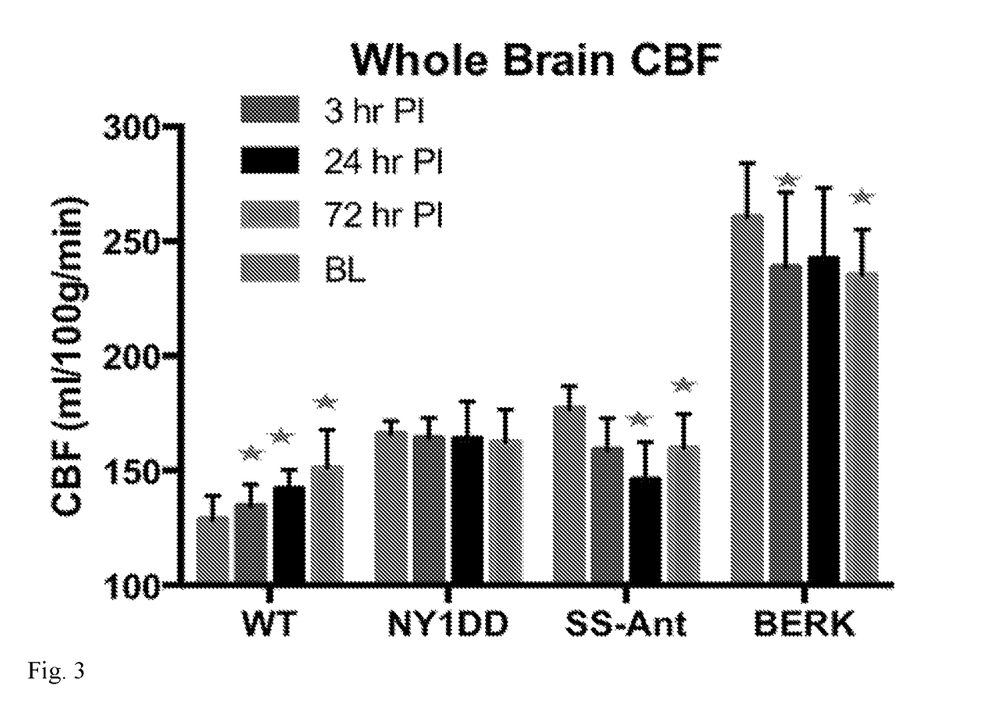
FIG. 3: Whole Brain CBF before (baseline, BL) and after (PI, post injection) 10% top-load with EAF-P5K6-Alb. CBF increased in WT animals, but decreased in SS-Antilles and BERK animals. * indicated p<0.001 W.R.T BL.
Figure 4:
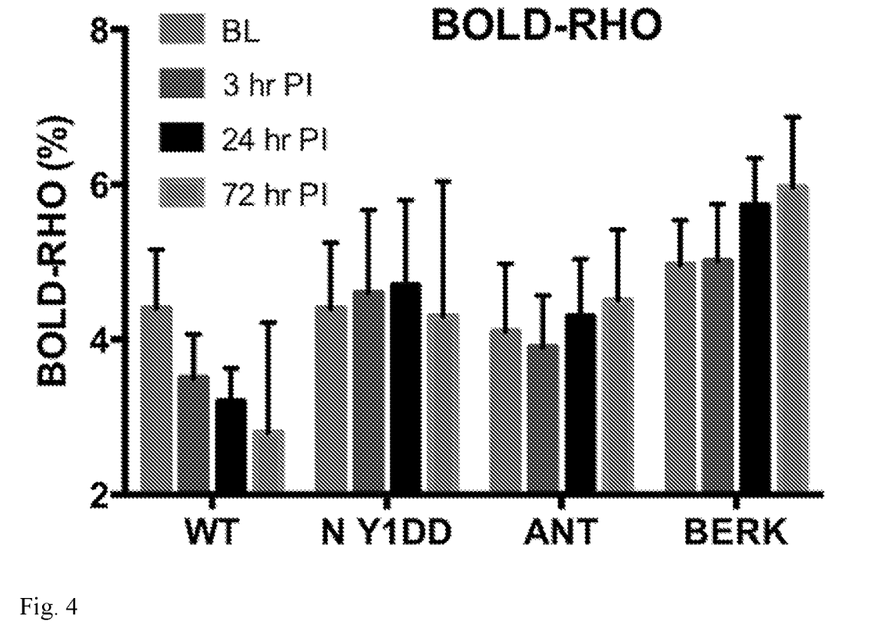
FIG. 4: BOLD-RHO (gray matter) Response to Hyperoxia in WT and SCD Models. BL=baseline, PI=post injection. WT BOLD-RHO decreased, while BERK mice exhibited increased deoxyHb level in response to Hyperoxia.

In normal (wild type) animals, EAF-PEG-Alb substantially increases CBF (FIG. 3, left). However, in sickle transgenic animals, the drug significantly reduces leukocyte adhesion in systemic post capillary venules and increase vessel flow in systemic tissue. These effects are coupled with a significant decrease in CBF (FIG. 3, far right) leading to a consequent increase in cerebral hypoxia, increased cerebral oxidative stress and stroke (FIG. 4). This decrease in CBF is also associated with a decrease in cerebral oxygen delivery, resulting in post-drug administration increases in cerebral hypoxia. Using BOLD MRI imaging (which is sensitive to the tissue concentration of deoxy-Hb) the sufficiency of oxygenation of cerebral tissues was measured by assessing the change in deoxy-Hb which occurs with administration of a short inhalation bolus of 100% O2. The measure, termed BOLD-RHO (FIG. 4) indicates adequacy of oxygen delivery to the tissues. As indicated in FIG. 4, the decrease in CBF which followed administration of EAF-PEG-Alb in BERK mice was accompanied by increased hypoxic stress (FIG. 4, far right. Note that WT animal Hypoxic stress decreases, as the increasing flow experienced represents a "luxury" perfusion increase).

As described above, the anti-sickling effect of the EAF-PEG-Alb leads to rapid increase in systemic capillary filling, a consequent decrease in MAP and a consequent drop in cerebral perfusion pressure resulting in a drop in CBF.

Figure 5:
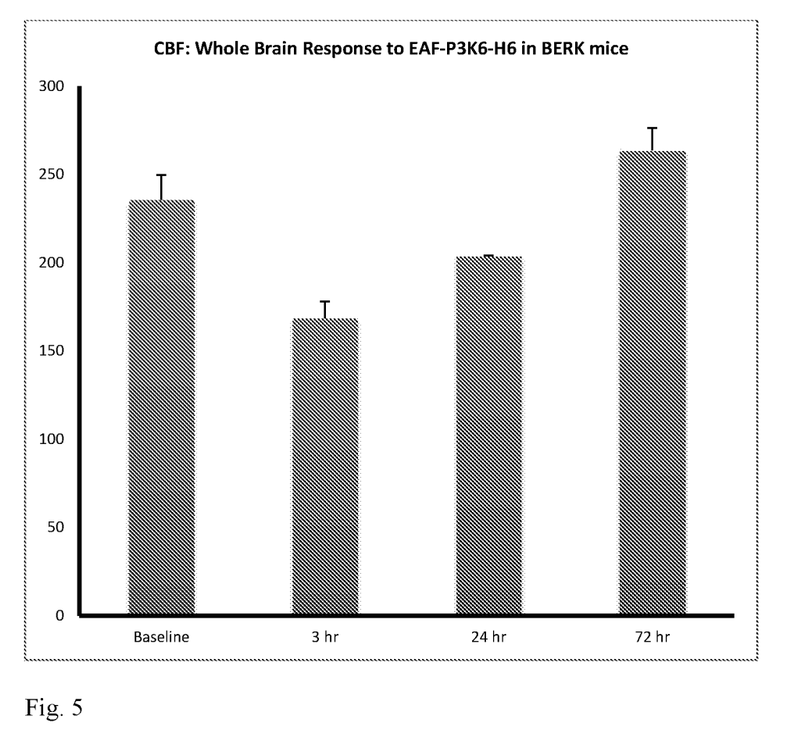
FIG. 5: CBF Response in BERK mice at different times following administration of EAF-PEG-Hb. The same drop in CBF was observed following administration of EAF-PEG-Hb that was observed following EAF-PEG-Alb, indicating that antisickling therapy was successful, but the decrease in CBF followed decreases in MAP.
Figure 6:
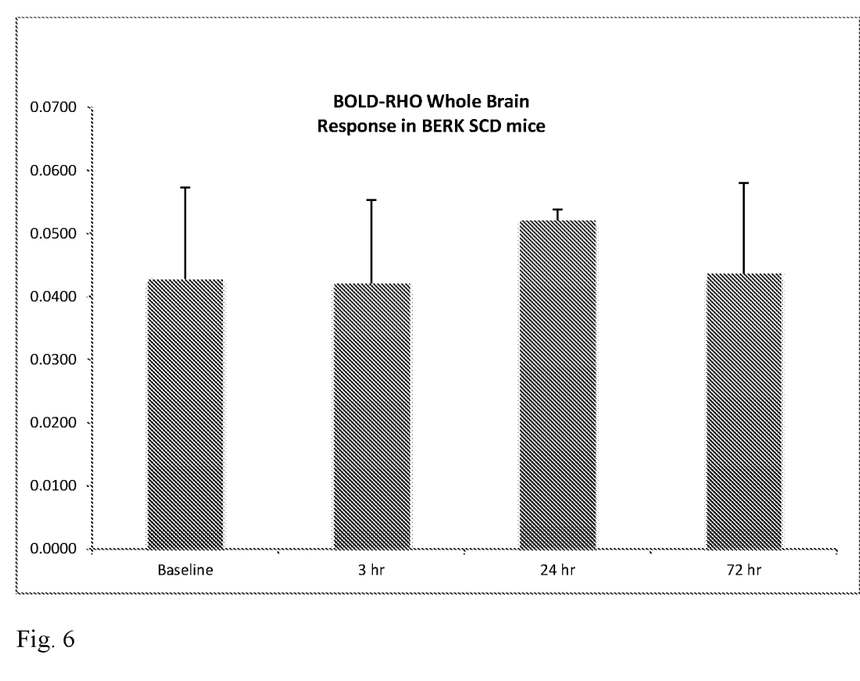
FIG. 6: BOLD-RHO Response in BERK mice at different times following administration of EAF-PEG-Hb. No drop in brain deoxy-Hb was detected, indicating that the addition of oxygen carrying Hb to the EAF-PEG formulation protected the brain from the drop in CBF accompanying antisickling therapy.

When the Albumin in the supra-plasma expander is replaced with hemoglobin (EAF-PEG-Hb), peripheral leukocyte adhesion is still reduced and peripheral flow is still increased, and consequently CBF is also decreased. This is illustrated in FIG. 5, which demonstrates the expected decrease in CBF. However, unlike EAF-PEG-Alb, the substitution of Alb with Hb in the molecule imparts increased oxygen carrying/delivering capacity to the blood, resulting in reduced likelihood for cerebral sickling and reduced cerebral oxidative stress to the brain. However, unlike the situation following administration of EAF-PEG-Alb, the brain is protected against the decrease in CBF following EAF-PEG-Hb by the extra oxygen being delivered by the EAF-PEG-Hb (FIG. 6). This effect is achieved with only a 10% top-load of the compound to the animal, demonstrating that even a small improvement in oxygen carrying capacity using a high oxygen affinity supra-perfusion resuscitation fluid, can protect against the decrease in CBF which ensues following anti-sickling therapy. This effect can be achieved by combination of any therapy with EAF-PEG-Hb.

Just as with supra-perfusion therapy, a sickle therapy induced toxicity is apparent in the quercetin-based antioxidant therapy of sickle cell disease. The chronic state of the sickle disease in BERK low gamma as reflected by vaso-occlusion can be nearly completely attenuated by a 200 mg/kg of quercetin given intraperitonially and therapeutic efficacy measured after 3 hrs of infusion of the therapeutic, and this therapeutic efficacy is dose dependent. However, this nearly complete clearance of the vaso-occlusion appears to induces a toxicity to such treated low gamma BERK, as the animal die after six to eight hrs. after infusing quercetin. Accordingly, it was concluded that antisickling, or antioxidant or antiadhesive therapies, need to be combined with anti-anemia therapy to protect the brain tissues from hypoxic effects as the systemic perfusion is improved as vasoconstrictive effects are reduced.

However, if the therapy is pursued, with a lower intraperitoneal dosing of quercetin, 50 mg/kg dose three times a week, the small attenuation of vaso-occlusion seen with this lower dosage in BERK low gamma is not toxic to animals even after seven weeks of treatment. Such a therapy has a very little influence, however, on the CBF of the BERK mouse. A lower dosage of the therapeutic that only marginally reduces the severity of the disease as reflected by systemic vaso-occlusion can still moderate the severity of the disease to some degree without creating an oxygen debt in the brain (i.e. the pathology of the disease as reflected by CBF and BOLD, in an organ specific manner). Indeed, a daily oral dosing of quercetin at 100/mg per/kg for 10 days to low gamma BERK and attenuates the vaso-occlusion more than 50%, and improves the systemic circulation by 60 to 70%, but without any significant influence on CBF or BOLD.

The therapeutic efficacy of quercetin is unique and novel, a multifunctional therapeutic for SCD. That level of therapeutic efficacy is not seen with iso-quercetin or mangiferine, closely related antioxidants.

The reduction in the vaso-occlusion seen with that amount of oral dosing of quercetin is comparable to that in medium gamma BERK, with about 10 to 25% fetal Hb expression. This level of fetal Hb is generally the targeted level for hydroxyurea therapy. This level of fetal Hb has only a marginal influence on the CBF as compared to low gamma. The normalization of CBF is seen in high gamma BERK, which has an expression of fetal Hb to a level of about 30 to 40%.

Though hydroxy urea therapy has been developed as an anti-sickling approach that induces the expression fetal Hb, it is becoming apparent that hydroxy urea is a multifuctional therapeutic approach: (i) anti-sickling effect by inhibition of polymerization of deoxy HbS (ii) anti-anemia effect by targeting the tissue oxygenation of the hypoxia regions thereby reducing the complete deoxygenation of oxy-HbS in vivo (iii) an antioxidant effect, substituted hydroxyls have been shown to exhibit antioxidant activity in vivo. Indeed an infusion of a single dose of 20 mg/kg of hydroxy urea to low gamma BERK intraperitoneally reduces the vaso-occlusion to level close to that of medium gamma BERK with a significant improvement in systemic flow in just three hrs. after infusion, without any expression of fetal Hb. A similar effect of hydroxy urea is expected for oral dosing of hydroxyurea as well.

Accordingly, a combination therapy for SCD using quercetin and hydroxyurea, both given orally is provided.

Infusion of a 6 gm % solution EAF P3K6 Hb to a low gamma BERK mice at 10% top load results in a presence of 0.3 gm/dl EAF P3K6 Hb in the plasma, the HbS in the RBC being 8 gm/dl. The small amount of PEG Hb is able to normalize the CBF. On the other hand the presence of 10 to 20% of fetal Hb as seen in medium gamma BERK has only a limited influence on the CBF. Supra-perfusion resuscitation property of EAF P3K6 Hb facilitates the transfer of oxygen from RBC to tissues, a catalytic activity of EAF PEG Hb The anti-anemia effect of PEG Hb in the plasma (as reflected by the normalization of CBF in low gamma BERK) is considerably superior to high oxygen affinity Hb in RBC.

What is claimed is:

1. A method of reducing cell sickling and preventing a cerebral tissue pathology in a subject having a sickle cell disease with vaso-occlusion comprising:
    administering a 10% top-load of a pegylated hemoglobin (PEG-Hb) molecule having a higher oxygen affinity than hemoglobin in red blood cells to the subject, wherein the PEG-Hb molecule reduces cell sickling and is sufficient to protect against a cerebral tissue pathology caused by a reduced cerebral blood flow (CBF) that results from administering the 10% top-load to treat the sickle cell disease with vaso-occlusion in the subject; and
    administering an amount of 5-hydroxyl methyl furfural or a composition comprising red blood cells ex vivo treated with 5-hydroxyl methyl furfural to the subject.

2. The method of claim 1, wherein the cerebral tissue pathology is cerebral hypoxic insult.

3. The method of claim 1, wherein the PEG-Hb molecule comprises a hemoglobin molecule having 6 molecules of 3,000 mw polyethylene glycol (PEG) attached thereto (P3K6 Hb).

4. The method of claim 3, wherein the P3K6 Hb is extension arm facilitated P3K6 Hb (EAF P3K6 Hb).

5. The method of claim 3, wherein the P3K6 Hb is an antioxidant adduct of EAF P3K6 Hb.

6. The method of claim 5, wherein the antioxidant is a flavonoid.

7. The method of claim 1, further comprising administering a pegylated albumin (PEG-Alb) molecule.

8. The method of claim 1, further comprising administering an amount of a quercetin to the subject.

9. The method of claim 5, further comprising orally administering an amount of hydroxyl urea to the subject.

10. A method of reducing cell sickling and preventing a cerebral tissue pathology in a subject having a sickle cell disease with vaso-occlusion comprising:
    administering a 10% top-load of an EAF P3K6-Hb molecule to the subject, wherein the PEG-Hb molecule reduces cell sickling and is sufficient to protect against a cerebral tissue pathology caused by a reduced cerebral blood flow (CBF) that results from administering the 10% top-load to treat the sickle cell disease with vaso-occlusion in the subject.

* * * * *